US 8,332,236 B2

(12) United States Patent
Yurko et al.

(10) Patent No.: US 8,332,236 B2
(45) Date of Patent: *Dec. 11, 2012

(54) METHOD AND SYSTEM FOR TRACKING AND MONITORING PATIENT COMPLIANCE WITH MEDICAL DEVICE USAGE PRESCRIPTION

(75) Inventors: Gregory Yurko, Murrysville, PA (US); Kevin Bowen, Pittsburgh, PA (US); Mark D'Angelo, Harrison City, PA (US); Rochelle Eisert, Pittsburgh, PA (US); Michael H. Kissel, Harrison City, PA (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/004,412

(22) Filed: Jan. 11, 2011

(65) Prior Publication Data
US 2011/0112857 A1    May 12, 2011

Related U.S. Application Data

(63) Continuation of application No. 10/645,114, filed on Aug. 21, 2003, now Pat. No. 7,890,342.

(60) Provisional application No. 60/406,247, filed on Aug. 21, 2002.

(51) Int. Cl.
G06Q 10/00 (2006.01)
G06Q 50/00 (2006.01)
A61B 5/00 (2006.01)
G06F 19/00 (2006.01)

(52) U.S. Cl. .............................. 705/2; 705/3

(58) Field of Classification Search ............ 705/2–3
See application file for complete search history.

(56) References Cited

U.S. PATENT DOCUMENTS

| | | | |
|---|---|---|---|
| 5,284,133 A * | 2/1994 | Burns et al. | 128/200.23 |
| 5,359,513 A * | 10/1994 | Kano et al. | 382/128 |
| 5,517,983 A | 5/1996 | Deighan | |
| 5,706,801 A * | 1/1998 | Remes et al. | 128/202.26 |
| 5,715,812 A | 2/1998 | Deighan | |
| 5,740,795 A | 4/1998 | Brydon | |
| 6,249,717 B1 * | 6/2001 | Nicholson et al. | 700/241 |
| 6,578,003 B1 * | 6/2003 | Camarda et al. | 705/3 |
| 2003/0221687 A1 | 12/2003 | Kaigler | |

OTHER PUBLICATIONS

Kribbs et al., "Objective Measurement of Patterns of Nasal CPAP Use by Patients With Obstructive Sleep Apnea", Am Rev Respir Dis, 1993, vol. 147, pp. 887-895.*

(Continued)

*Primary Examiner* — Robert Morgan
*Assistant Examiner* — Joy Chng
(74) *Attorney, Agent, or Firm* — Michael W. Haas (57) ABSTRACT

A computer-implemented method for tracking and monitoring a patient's compliance with a medical device usage prescription for a medical device is disclosed. This method and system includes the steps of: (a) providing a minimum medical device usage compliance value for the medical device for a predetermined compliance period; (b) providing the quantity of compliance periods in a measurement cycle; and (c) determining a compliance period value as the number of compliance periods in the measurement cycle in which an actual medical device usage value is at least equal to the minimum medical device usage compliance value. In another embodiment, the method also includes: providing a weighting factor, and applying the weighting factor to at least one actual medical device session usage value.

24 Claims, 2 Drawing Sheets

OTHER PUBLICATIONS

Kribbs et al., "Objective Measurement of Patterns of Nasal CPAP Use by Patients with Obstructive Sleep Apnea", Am Rev Respir Dis., 1993 vol. 147, pp. 887-895.

Respironics, Inc., "Treatment, Compliance, and Outcomes Module, Sleep Management Program", Overview and Section 2—"Patient Set-Up and Education", 2000.

* cited by examiner

METHOD AND SYSTEM FOR TRACKING AND MONITORING PATIENT COMPLIANCE WITH MEDICAL DEVICE USAGE PRESCRIPTION

CROSS-REFERENCE TO RELATED APPLICATIONS

This application is a Continuation application under 35 U.S.C. §120 of U.S. patent application Ser. No. 10/645,114, filed Aug. 21, 2003 which priority under 35 U.S.C. §119(e) from provisional U.S. patent application No. 60/406,247 filed Aug. 27, 2002 the contents of which are incorporated herein by reference.

BACKGROUND OF THE INVENTION

1. Field of the Invention

The present invention relates to a method and system for tracking and managing a patient's compliance with a medical treatment regimen or prescription, and, in particular, to a method and system that tracks and manages a patient's compliance with a prescribed usage of a medical device.

2. Description of the Related Art

It is well known to treat a medical disorder or to diagnose, treat or monitor the condition of a patient using medical equipment. For example, patients suffering from a pulmonary or respiratory disorder, such as obstructive sleep apnea (OSA), are often treated with a pressure support device, such as a continuous positive airway pressure (CPAP) device. A CPAP device delivers a flow of fluid to the airway of the patient throughout the patient's breathing cycle in order to "splint" the airway, thereby preventing its collapse during sleep. Examples of such CPAP devices are the REMstar® and Solo® family of CPAP devices manufactured by Respironics, Inc. of Pittsburgh, Pa.

It is also known to provide a bi-level positive pressure therapy, in which the pressure of fluid delivered to the patient's airway varies or is synchronized with the patient's breathing cycle to maximize the medical effect and comfort to the patient. An example of pressure support devices that provide "bi-level" pressure support, in which a lower pressure is delivered to that patient during the patient's expiratory phase than during the inspiratory phase, is the BiPAP® family of devices manufactured and distributed by Respironics, Inc. of Pittsburgh, Pa. Such a bi-level mode of pressure support is taught, for example, in U.S. Pat. No. 5,148,802 to Sanders et al.; U.S. Pat. No.5,313,937 to Zdrojkowski et al.; U.S. Pat. No. 5,433,193 to Sanders et al.; U.S. Pat. No. 5,632,269 to Zdrojkowski et al.; U.S. Pat. No.5,803,065 to Zdrojkowski et al.; and U.S. Pat. No. 6,029,664 to Zdrojkowski et al., the contents of each of which are incorporated by reference into the present invention.

It is further known to provide an auto-titration positive pressure therapy in which the pressure provided to the patient changes based on the detected conditions of the patient, such as whether the patient is snoring or experiencing an apnea, hypopnea, or upper airway resistance. An example of a device that adjusts the pressure delivered to the patient, based on whether or not the patient is snoring, is the Virtuoso® CPAP family of devices manufactured and distributed by Respironics, Inc. An example of a pressure support device that actively tests the patient's airway to determine whether obstruction, complete or partial, could occur and adjusts the pressure output to avoid this result is the Tranquility® Auto CPAP device, also manufactured and distributed by Respironics, Inc. An exemplary auto-titration pressure support mode is taught, for example, in U.S. Pat. Nos. 5,203,343; 5,458,137; and 6,087,747, all to Axe et al., the contents of which are incorporated herein by reference. A further example of an auto-titration pressure support device that actively tests the patient's airway to determine whether obstruction, complete or partial, could occur and adjusts the pressure output to avoid this result is the Tranquility® Auto CPAP device, also manufactured by Respironics, Inc. This auto-titration pressure support mode is taught in U.S. Pat. No. 5,645,053 to Remmers et al., the content of which is also incorporated herein by reference.

In treating a patient using any of the above-described pressure support systems, each of which represents a mode of providing pressure support, it is often desirable to monitor various parameters associated with the use of such systems. Once a patient is diagnosed with a breathing disorder, he or she is typically prescribed a pressure support therapy, i.e., a mode of pressure support (CPAP, bi-level, or auto-titration) and given a prescribed pressure support level. The pressure support therapy (mode of pressure support and pressure settings) is typically prescribed by a physician after the patient undergoes a sleep study at a sleep lab. The patient's healthcare provider, such as that patient's physician or health insurance company, is often interested in ensuring that the patient actually uses the pressure support therapy as prescribed. Thus, it is known to monitor a patient's compliance with the prescribed therapy by monitoring the patient's usage of the pressure support device.

Typically, a doctor or other health care provider is able to track and monitor a patient's compliance with the prescribed pressure support device usage by tracking the operation of the prescribed pressure support device. In addition, a status monitor may be in communication with the respiratory apparatus that delivers breathable gas to the airway of a patient. The status monitor determines the status of the usage of the unit by the patient and includes a timer for determining the accumulated time of usage of the unit by the patient. See, e.g., U.S. Pat. No. 5,517,983 to Deighan et al. As shown in U.S. Pat. No. 5,706,801 to Remes et al., such compliance monitors also may have remote communication functionality, allowing the usage information to be transmitted from the device to a remote computer.

However, these conventional compliance monitoring systems are deficient in that they measure only the operational or device usage time, whether through device operation, cannula operation, air flow measurement, etc. These devices then provide a total usage time, from which the device or a remote computer calculates the compliance with the prescribed total usage time. The measurement and compliance monitoring is a strictly static one and only provides limited "snap shots" demonstrating compliant or non-compliant behavior. Therefore, there remains a need for a method and system for dynamically tracking and monitoring a patient's compliance with a prescribed device usage allotment during a cycle of predetermined periods.

Another deficiency evident in the conventional compliance monitoring methods and systems stems from their definition of "compliance." In other words, these systems track, monitor, and manage a "technical" compliance level for a patient. For example, if a patient is prescribed a device usage time of eight hours of usage in a 24-hour period, the mere fact that the patient uses the device for 8 hours during that period does not necessarily indicate that the patient is "compliant." In prior art systems, any usage of the device is accrued towards the prescription level.

However, relatively short usage sessions, e.g., sessions where the medical device is used continuously for ten or twenty-minutes or less, may not effectively treat the patient. This is because a person with normal sleeping patterns will go through a cycle of different stages of sleep during the course of a night. The cycle for a particular person is a sequence of these stages, usually in the same order, with a relatively constant time in each stage. Any disruption causes this normal pattern to be disturbed, resulting in a reduction of time in each stage of sleep, which can have negative effects on health. Short sessions indicate that the patient is waking frequently and thus creating this disruption of normal sleep patterns. Therefore, there remains a need for a compliance method and system that ensures that the patient is meeting an actual compliance level, as opposed to a "technical" compliance level.

SUMMARY OF THE INVENTION

It is, therefore, an object of the present invention to provide a method and system for tracking and monitoring patient compliance with a medical device usage prescription that overcomes the deficiencies of the prior art. It is another object of the present invention to provide a compliance monitoring method and system that tracks a patient's compliance over various predetermined compliance periods and measurement cycles. It is yet another object of the present invention to provide a method and system for tracking and monitoring patient compliance, which tracks a patient's "actual" compliance, as opposed to mere "technical" compliance. It is a still further object of the present invention to provide a method and system for tracking and monitoring a patient's compliance with a therapeutic device usage prescription or regimen.

The present invention is a method and system for tracking and monitoring a patient's compliance with a medical device usage prescription. The method is a computer-implemented method and includes the steps of: (a) providing a minimum medical device usage compliance value for the medical device for a predetermined compliance period; (b) providing the quantity of compliance periods in a measurement cycle; and (c) determining a compliance period value as the number of compliance periods in the measurement cycle in which an actual medical device usage value is at least equal to the minimum medical device usage compliance value.

In a preferred embodiment, the method also includes the steps of: (a) providing a weighting factor; and (b) applying the weighting factor to at least one actual medical device session usage value. In this embodiment, the weighting factor can be selected such that the session usage value is discarded entirely (weighting factor=0) or reduced based on the duration of the session usage value.

In another preferred embodiment, the method includes the steps of: (a) providing a minimum medical device usage short session value; (b) comparing the actual medical device usage value for a discrete usage session with the minimum medical device usage short session value; and (c) determining a short session count value based upon the number of usage sessions wherein the actual medical device usage value for the respective usage session is less than the minimum medical device usage short session value.

These and other objects, features and characteristics of the present invention, as well as the methods of operation and functions of the related elements of structure and the combination of parts and economics of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
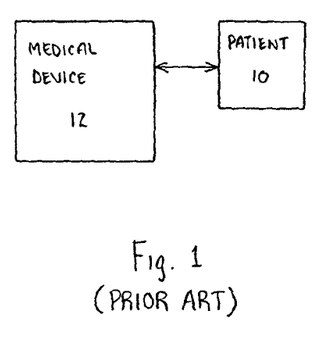
FIG. 1 is a schematic view of a patient/medical device relationship according to the prior art.

The present invention is directed to a computer-implemented method and system for tracking and monitoring patient compliance with a medical device usage prescription. As seen in FIG. 1, a patient 10 may use a medical device 12 on an on-going or periodic basis, in order to assist or complement the healing or treatment process. Typically, such a medical device 12 would be referred to as a "therapeutic" device and includes its associated equipment. Examples of therapeutic or medical devices 12 (and inclusive equipment) include a ventilator, a pressure support system (CPAP, bi-level device, auto-titration device, etc.,) an oximeter, a ventilatory support system, an oxygen concentrator, a nebulizer or humidifier, a phototherapy device, an immersion therapy device, and a physical therapy device. For purposes of the present invention, medical device 12 or therapeutic device includes an apparatus capable of performing the method for the compliance tracking and monitoring method and an apparatus for controlling and executing this method.

The method and system of the present invention allows a user to track and monitor a patient's 10 compliance with a medical device usage prescription for a medical device 12. This method includes the steps of: (a) providing a Minimum Medical Device Usage Compliance Value for medical device 12 for a predetermined Compliance Period; (b) providing the quantity of Compliance Periods in a Measurement Cycle; and (c) determining a Compliance Period Value as the number of Compliance Periods in the Measurement Cycle in which an Actual Medical Device Usage Value is at least equal to the Minimum Medical Device Usage Compliance Value.

Typically, a doctor or caregiver will prescribe a Medical Device Usage Prescription Value. For purposes of the present invention, the "Medical Device Usage Prescription Value" is defined as the period of time, typically expressed as a number of hours, that the medical device should be used on a relatively continuous basis by the patient during a Compliance Period. The "Compliance Period" is the period of time over which one or more Usage Sessions are measured. A "Usage Session" is a period of time, typically expressed as a number of minutes or hours, during a Compliance Period in which the medical device is used in a continuous basis by the patient. It can be appreciated that during each Compliance Period the patient will participate in at least one Usage Session.

A doctor, for example, may prescribe that patient 10 use medical device 12, such as a pressure support system, for eight hours in a day. In treating OSA with a CPAP therapy, the eight hour period is typically at night while the patient is asleep. In this hypothetical example, the "Medical Device Usage Prescription Value" is eight hours and the "Compliance Period" is 24 hours or one day.

It can be appreciated that this is the ideal prescription for providing the maximum beneficial effect to patient 10. However, as is common with medical prescriptions, it is often unlikely that the patient will meet the prescribed value or level on a consistent basis. For example, when the doctor prescribes that patient 10 use medical device 12 for at least eight hours during a 24-hour period, patient 10 may use medical device 12 much less often, i.e., not every day, for much shorter periods of time, i.e., not for the full eight hours each day, or both.

In monitoring and tracking patient 10 usage of medical device 12, it is common to assign a Minimum Medical Device Usage Compliance Value for medical device 12. The "Minimum Medical Device Usage Compliance Value" is defined as the minimum level of usage required during a Compliance Period, below which the benefit of the medical device begins to diminish. This value is typically set by a physician, caregiver, or other healthcare professional or medical device manufacturer and may be patient specific, device specific, or both. In the above example, while patient 10 has been prescribed an 8-hour treatment regimen, for compliance monitoring, the doctor may also estimate the Minimum Medical Device Usage Compliance Value, below which the benefit of medical device 12 begins to diminish. For example, given the above-discussed 8-hour prescription, the doctor may set the Minimum Medical Device Usage Compliance Value for medical device 12 at four hours for any given Compliance Period, which, in this case, is a day or twenty-four hours.

After setting the Minimum Medical Device Usage Compliance Value for medical device 12 for the Compliance Period, the user or doctor would decide how many Compliance Periods are in a Measurement Cycle. A "Measurement Cycle" is defined as the period of time or number of compliance periods over which the patient is to be monitored to indicate actual compliance with the prescribed therapy. In the preferred embodiment, where the Compliance Period is twenty-four hours, the Measurement Cycle could be a week (seven days) or seven Compliance Periods. It can be appreciated that the Measurement Cycle is not fixed for all patients and all medical therapies. Rather, the Measurement Cycle would be determined by the physician, caregiver, or other health care provider as being a period of time over which monitoring the patient's compliance would provide meaningful information regarding the usage by the patient in effectively treating the condition of interest.

Finally, the Compliance Period Value is determined as the number of Compliance Periods (e.g., 24-hour periods) in the Measurement Cycle (e.g., seven 24-hour Compliance Periods) where an Actual, i.e., measured, Medical Device Usage Value is equal to or greater than the set Minimum Medical Device Usage Compliance Value. The "Actual Medical Device Usage Value" is defined as an actual measurement of device usage obtained using any conventional technique for monitoring such device usage. Again, returning to the above example, the Compliance Period Value would be a function of the number of 24-hour periods in the 7-day Measurement Cycle where the actual usage is equal to or higher than four hours.

After the Compliance Period Value is determined for the patient, the doctor or user can make an overall decision regarding patient's 10 compliance with some compliance value. For example, the doctor may compare the Compliance Period Value with the Medical Device Usage Prescription Value. This would be especially useful when the Minimum Medical Device Usage Compliance Value is equal to the Medical Device Usage Prescription Value.

A more often used formula converts the Compliance Period Value to a percentage of Compliance Periods in the Measurement Cycle in which the Actual Medical Device Usage Value is at least equal to the Minimum Medical Device Usage Compliance Value. This percentage is then compared to a set or commonly-used compliance percentage to determine whether the patient is compliant or non-compliant with his or her usage of the medical device.

Following are two examples of the present method when used in connection with a percentage compliance value:

EXAMPLE 1

Minimum Medical Device Usage Compliance Value=4 hours per Compliance Period
Compliance Period=24 hours
Measurement Cycle=7 Compliance Periods (i.e., 7 days)
Actual Medical Device Usage Value (1st Compliance Period)=5 hours
Actual Medical Device Usage Value (2nd Compliance Period)=6 hours
Actual Medical Device Usage Value (3rd Compliance Period)=2.5 hours
Actual Medical Device Usage Value (4th Compliance Period)=4 hours
Actual Medical Device Usage Value (5th Compliance Period)=5 hours
Actual Medical Device Usage Value (6th Compliance Period)=5.5 hours
Actual Medical Device Usage Value (7th Compliance Period)=4.5 hours The Compliance Period Value is 6, because there were 6 Compliance Periods during the Measurement Cycle where the Actual Medical Device Usage Value was greater than the Minimum Medical Device Usage Compliance Value (4 hours in this hypothetical). If "Compliance" is defined as exceeding the Minimum Medical Device Usage Compliance Value for at least 75% of the Measurement Cycle, the patient in this example is in compliance, because 6 out of 7 compliance periods for the measurement cycle corresponds to the ratio 6/7, which is equal to 86%.

EXAMPLE 2

Minimum Medical Device Usage Compliance Value=4 hours per Compliance Period
Compliance Period=24 hours
Measurement Cycle=7 Compliance Periods (i.e., 7 days)
Actual Medical Device Usage Value (1st Compliance Period)=5 hours
Actual Medical Device Usage Value (2nd Compliance Period)=6 hours
Actual Medical Device Usage Value (3rd Compliance Period)=2.5 hours
Actual Medical Device Usage Value (4th Compliance Period)=4 hours
Actual Medical Device Usage Value (5th Compliance Period)=5 hours
Actual Medical Device Usage Value (6th Compliance Period)=1 hour
Actual Medical Device Usage Value (7th Compliance Period)=4.5 hours Compliance Period Value is equal to 5, because there were 5 out of the 7 Compliance Periods where the Actual Medical Device Usage Value was greater than the Minimum Medical Device Usage Compliance Value (4 hours in this hypothetical). If "Compliance" is defined as exceeding the Minimum Medical Device Usage Compliance Value for at least 75% of the Measurement Cycle, the patient in this example is not in compliance, because 5 out of 7 compliance periods for the measurement cycle corresponds to the ratio 5/7, which is equal to 72%.

In order to determine compliance, the present invention also contemplates inputting or providing the Actual Medical Device Usage Value for each Compliance Period, as well as a Measurement Cycle Compliance Value, and comparing the resulting Compliance Period Value with the Measurement Cycle Compliance Value. In the above two examples, the Measurement Cycle Compliance Value is set at 75%. The Measurement Cycle Compliance Value can be considered as a value, typically expressed as a percentage or period of time, during the Measurement Cycle, below which the benefit of the medical device begins to diminish.

After the comparison, a Compliance Indicator is provided, based upon the results. Again, in the above examples, the Compliance Indicator would indicate a "compliance" for the first example and a "non-compliance" for the second example. Typically, the Compliance Indicator indicates a "compliance" signal if the Compliance Period Value is at least equal to the Measurement Cycle Compliance Value and a "non-compliance" signal if the Compliance Period Value is less than the Measurement Cycle Compliance Value. This Compliance Indicator may also indicate, in addition to the "compliance" signal and the "non-compliance" signal, a "marginal compliance" signal, a "warning" signal, a "trend" signal and a "compliance value" signal.

It is also envisioned that a report can be created based upon the Compliance Indicator. Such a report would be indicative of patient 10 compliance with the Medical Device Usage Prescription Value, the Minimum Medical Device Usage Compliance Value, the Measurement Cycle Compliance Value, etc. This report can be in the form of a list, a chart, a diagram, a graph, etc., and generated and presented using any conventional technique.

The above calculations typically lead to a very simple and non-explanatory "compliance" or "non-compliance" label. However, the present method can be adjusted, by adjusting the Minimum Medical Device Usage Compliance Value, the Compliance Period, and the Measurement Cycle to provide a variety of measures and trends towards compliance or non-compliance. When adjusting the above variables, for example decreasing the Measurement Cycle, the doctor, caregiver or user can use this method in a preventative manner.

For example, a Compliance Warning Value could be provided, and the Compliance Period Value compared with the Compliance Warning Value. This could be done on, for example, a daily basis. When the Compliance Period Value equals the Compliance Warning Value, a warning signal could be presented to both patient 10, as well as the doctor or caregiver. At this point, patient 10 could attempt to adjust his or her usage of medical device 12. Additionally, the doctor or caregiver could contact patient 10 and notify them of their movement towards non-compliance, which results in minimal and often zero benefit by the patient usage of medical device 12.

It is envisioned that this Compliance Warning Value can be set by a user, and the user could be a patient, a doctor, a caregiver, a medical device manufacturer, etc. Further, the warning signal can be an audible alarm or a visual display. The visual display could include an alphanumeric message, and this alphanumeric message could be user-defined. For example, medical device 12 could provide an audible alarm or a message on its display informing patient 10 of his or her non-compliant use of medical device 12.

The Compliance Period could also be defined or referred to as a prescription period. This prescription period can be a 12-hour period, a 24-hour period, a multi-day period, a weekly period, a multi-weekly period, a monthly period, a multi-monthly period, an annual period and/or a multi-yearly period. Further, the Compliance Period could be a static period, a rotating period or a dynamic period. Similarly, the Measurement Cycle can be a 12-hour period, a 24-hour period, a multi-day period, a weekly period, a multi-weekly period, a monthly period, a multi-monthly period, an annual period and/or a multi-yearly period.

In determining the Actual Medical Device Usage Value, typically this value is based upon the operation of one or multiple components of the medical device. For example, this value can be determined by the operation or power-consumption of a blower, a battery, a power input, a motor, etc. Additionally, the Actual Medical Device Usage Value can be based upon a measured physical parameter indicative of a patient's actual usage of the medical device, such as a flow rate, a pressure differential, a temperature, a density, a mass analysis, a constituent identification, etc.

Figure 2:
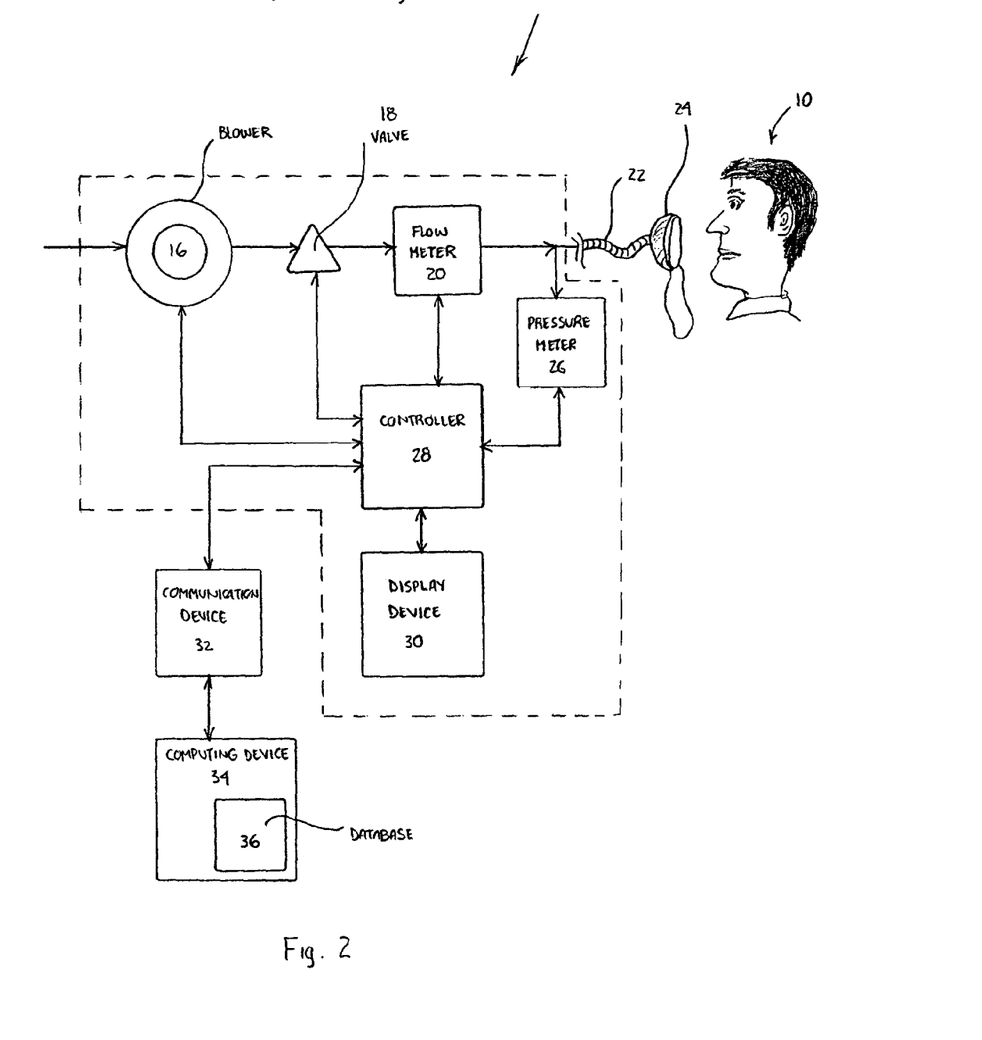
FIG. 2 is a schematic view of a pressure support system employing the method and system according to the present invention.

As seen in FIG. 2, the present invention contemplates using the compliance monitoring techniques discussed above in connection with a pressure support system 14 corresponding to medical device 12. Pressure support system 14 includes a blower 16, which intakes air, pressurizes the air and exhausts the air through a valve 18 further through a flow meter 20, through tubing 22 and into a patient interface device 24, such as a nasal mask. Patient interface device 24 is placed over the nose, mouth, or both of patient 10 and, in this manner, the patient receives air at a pressure greater than the ambient pressure from pressure support system 14. A pressure meter 26 may also be connected to the air flow or tubing 22, which is also know in the art at the patient circuit.

It should be noted that other conventional configurations of pressure support system 14 are contemplated by the present invention. For example, it is known to eliminate valve 18 in favor of controlling the operating speed of blower 16 to control the pressure of gas delivered to the patient. It is also known to locate valve 18 upstream of blower 16. In addition, any combination of these alternative pressure support device would be suitable for use with the compliance monitoring techniques of the present invention.

Typically, all of blower 16, valve 18, flow meter 20, and pressure meter 26 are connected to a controller 28. Controller 28 controls the various components of the pressure support system, and also may include appropriate software to complete one or more of the steps and sub-steps of the present method. In addition, controller 28 can be in communication with a display device 30, which may display any of the results or values of the variables discussed above for viewing by patient 10.

While display device 30 may provide information to the patient, controller 28 may also be in communication with a communication device 32, such as a modem. Communication device 32 can be either internal, integrated or external to pressure support system 14. In addition, communication device 32 is in communication with a remote computing device 34, and this remote computing device 34 may contain a central database 36 thereon.

Medical device 12, and in this case a pressure support system 14, communicates with remote computing device 34 via a user, a direct link, a telecommunications data link, a temporary storage medium, etc. Further, any of the information and data discussed above can be transmitted by communication device 32 to computing device 34, and, specifically, to database 36 on computing device 34. For example, the communication device may transmit the Minimum Medical Device Usage Compliance Value, the Compliance Period, the Measurement Cycle, the Compliance Period Value, the Actual Medical Device Usage Value, the Medical Device Usage Prescription Value, the Measurement Cycle Compliance Value, the Compliance Indicator, the compliance warning signal, the compliance signal, the non-compliance signal, the marginal compliance signal, the trend signal, the compliance value signal, the Compliance Warning Value, the medical device operation signal, the measured physical parameter, the flow rate, the pressure signal, the temperature, the density, the mass analysis, and/or the constituent identification. All of this information and data can be stored as data fields on central database 36. It is also envisioned that this central database 36 can be resident on a computing system, a home care provider network, a primary care provider network, an insurance network, a manufacturer network, etc.

In another embodiment of the present invention, the method of monitoring patient compliance includes determining the Actual Medical Device Usage Value for the Compliance Period based upon an Actual Medical Device Session Usage Value determined for each of multiple, discrete Usage Sessions. This Actual Medical Device Session Usage Value differs from the Actual Medical Device Usage Value, in that typically a patient will not use the medical device in only one, long compliant block of time. Instead, patient 10 will use medical device 12 in multiple and discrete smaller time blocks, referred to as Usage Sessions. As such, the Actual Medical Device Usage Value is calculated as the sum of the Actual Medical Device Session Usage Values, which are accrued during the Compliance Period. However, such smaller blocks of time or Usage Sessions leads to a separate compliance problem. It should be noted that if the patient uses the medical device in only one long block of time during a Compliance Period, the Usage Session will be the same as the Compliance Period.

It can happen that if a patient uses the medical device for greater than the Minimum Medical Device Usage Compliance Value in any given Compliance Period, the compliance monitoring of the present invention described thus far, as well as conventional compliance monitoring methods, would consider patient 10 as being in compliance with the medical treatment. However, research indicates that extremely small or short usages of a medical device 12 provides a reduced benefit or even no benefit to the patient. Therefore, one embodiment of the present invention contemplates that relatively small or short usages of the medical device should not be included in the determination of compliance for that patient.

The present inventors also recognized that even short Usage Sessions may have some therapeutic value. However, the shorter the Usage Session, the greater the reduction in the beneficial effect of the medical device. For example, while patient 10 may not get the maximum therapeutic effect from medical device 12 if only used for a 40-minute session, he or she will get an even further reduced therapeutic effect for a 20-minute session. Therefore, in a further embodiment of the present invention, a Weighting Factor is applied to the Actual Medical Device Session Usage Value. Further, the Weighting Factor is variable and dependent upon the Actual Medical Device Session Usage Value, i.e., the value of the Weighting Factor is based on the length of the Usage Session.

In a preferred and non-limiting embodiment, the Weighting Factor ranges from zero to one. An exemplary preferred embodiment illustrating a relationship between the Weighting Factor and the duration of the Usage Session (a.k.a. Usage Session Value) is illustrated in a table format in FIG. 3. As seen in the table in FIG. 3, the patient is given zero "credit" towards his or her Actual Medical Device Session Usage Value if he or she has only used medical device 12 for up to twenty minutes. In the embodiment shown in FIG. 3, the Weighting Factor ranges between zero and one between an Actual Medical Device Session Usage Value ranging between twenty minutes and sixty minutes. After sixty minutes, the patient is given full credit for the time that medical device 12 was used in that Usage Session, i.e., a Weighting Factor of 1 is applied is the Usage Session is greater than or equal to sixty minutes.

Figure 3:
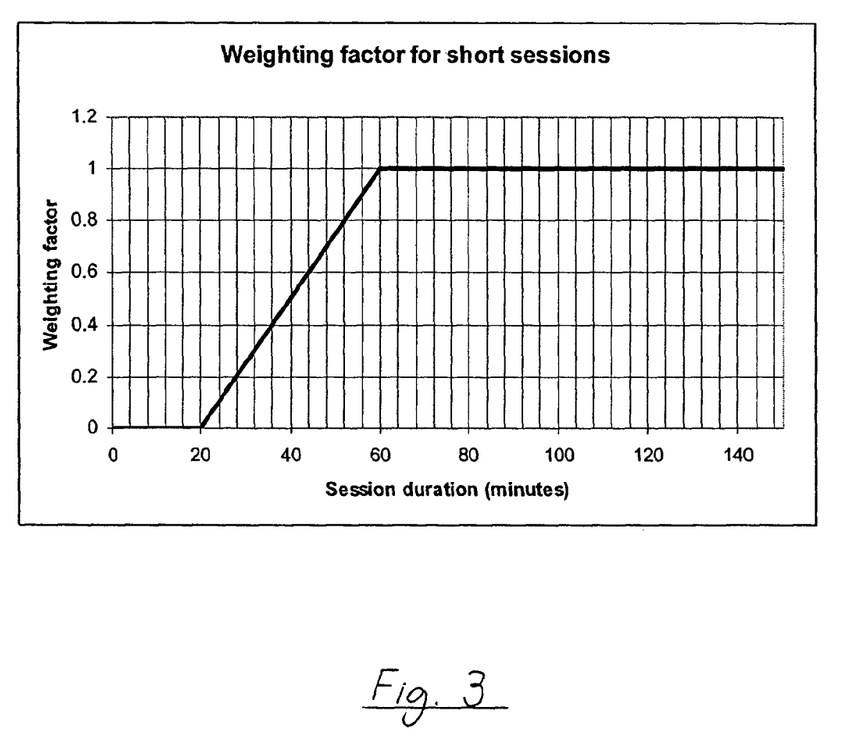
FIG. 3 is a chart of weighting factors for use in connection with short sessions according to the present invention.

It can be appreciated that the preceding embodiment of the present invention, where short usages of the medical device are not included in the determination of compliance for that patient, is the equivalent of making the Weighting Factor—Session Duration relation shown in FIG. 3 a step function, rather than a ramp function. The present invention contemplates than an infinite number of relations can be used for the Weighting Factor—Session Duration relation depending on how the length of the Usage Session is to impact on the inclusion of that Usage Session on the Actual Medical Device Usage Value for that Compliance Period. The present invention also contemplates that the Weighting Factor can be greater than 1 and less that zero. For example, the patient can be "penalized" if the Usage Session is too short or "rewarded" if the Usage Session is especially long.

The following is an example of how this Weighting Factor is applied using the Weighting Factor—Session Duration criteria set forth in FIG. 3.

EXAMPLE 3

Minimum Medical Device Usage Compliance Value=4 hours per Compliance Period
Compliance Period=24 hours
Measurement Cycle=7 Compliance Periods (days)
Actual Medical Device Usage Value (1st Compliance Period)
=5 hours
  Session Usage Value 1=20 minutes×Weighting Factor (0)=0 minutes
  Session Usage Value 2=40 minutes×Weighting Factor (0.5)=20 minutes
  Session Usage Value 3=2 hours×Weighting Factor (1)=2 hours
  Session Usage Value 4=40 minutes×Weighting Factor (0.5)=20 minutes
  Session Usage Value 5=20 minutes×Weighting Factor (0)=0 minutes
  Session Usage Value 6=1 hour×Weighting Factor (1)=1 hour
New Actual Medical Device Usage Value (TOTAL) for the first Compliance Period=3 hours and 40 minutes
For the rest of this example, it is assumed that the Actual Medical Device Usage Values in the remaining Compliance Periods were in at least 1 hour so that the Actual Medical Device Session Usage Values (wherein the Weighting Factor =1), are as follows:
Actual Medical Device Usage Value (2nd Compliance Period)=6 hours
Actual Medical Device Usage Value (3rd Compliance Period) =2.5 hours
Actual Medical Device Usage Value (4th Compliance Period) =4 hours
Actual Medical Device Usage Value (5th Compliance Period) =5 hours
Actual Medical Device Usage Value (6th Compliance Period) =5.5 hours Actual Medical Device Usage Value (7th Compliance Period) =4.5 hours Although the Actual Medical Device Usage Value for the 1st Compliance Period was actually 5 hours of total use, the appliance of the Weighting Factor to the "short session" usages moved the new Actual Medical Device Usage Value for the 1st Compliance Period to 3 hours and 40 minutes. Therefore, the previously compliant patient 10 (as illustrated in Example 1 due to the Compliance Period Value of 6/7) is now non-compliant, as follows:

Compliance Period Value=5/7 Compliance Periods>Minimum Medical

Device Usage Compliance Value (4 hours).

If "Compliance" is defined as exceeding the Minimum Medical Device Usage Compliance Value for at least 75% of the Measurement Cycle, the patient in this example is not in compliance, since 5/7=72%.

In another embodiment of the present invention, a Minimum Medical Device Usage Short Session Value can be provided, and the Actual Medical Device Usage Value for a discrete Usage Session can be compared with the Minimum Medical Device Usage Short Session Value. This comparison can yield a Short Session Count Value, which is an indication of the number of Usage Sessions where the Actual Medical Device Usage Value for the respective Usage Session (previously labeled as the Actual Medical Device Session Usage Value) is less than the Minimum Medical Device Usage Short Session Value.

The present invention contemplates providing Short Session Warning Value. The Short Session Count Value is compared with the Short Session Warning Value. A warning signal is presented to a user or caregiver when the Short Session Count Value equals or exceeds the Short Session Warning Value. As discussed above, this Short Session Warning Value may be set by a user, such as the doctor, caregiver, manufacturer, etc. The warning signal can be an audible alarm or a visual display, and the visual display may include an alphanumeric message. As discussed above, the alphanumeric message may be user-defined. This count of short sessions and warning if the number of short sessions exceeds a threshold, can be used alone or in combination with the weighting factor technique discussed above.

In the embodiments discussed above, only the length or duration of the Usage Session is used to determine whether the Usage Session Value for that Usage Session count toward the total compliance, and if so, whether the Usage Session Value will be weighted by some amount. The present invention, however, contemplates taking other criteria or events into consideration in evaluating the patient's Usage Sessions. The Weighting Factor can then be modified based on these other events.

In one exemplary embodiment, the present invention contemplates monitoring the physiological condition of the patient during a Usage Session and adjusting the Weighting Factor for that Usage Session based on the monitored condition of the patient. Monitoring the physiological condition of the patient can be done using any conventional technique in conjunction with pressure support system 14. For example, the present invention contemplates monitoring the flow of gas delivered to and received from the patient, the pressure of the flow of gas, the patient's muscle activity, the patient body position, and the patient's oxygen saturation. Also, the eye movement, brainwave activity, heart rate, or other criteria can be monitored, alone or in combination, to determine the condition of the patient, such as whether the patient is asleep and/or experiencing a certain sleep stage. If, for example, the patient is not asleep, this can be used to adjust the Weighting factor so as to reduce or eliminate (make the Weighting Factor=0) the contribution of the Usage Session Value associated with that Usage Session toward the Actual Medical Device Usage Value for that Compliance Period.

In another example, the patient is monitored to determine whether he or she is experiencing some respiratory related event, such as snoring, apnea, hypopnea, cheynes-stokes respiration, or rapid breathing. The Weighting Factor can be adjusted if one or more of these events are present during a Usage Session by applying an adjustment value on the Weighting Factor if a respiratory event is detected. In addition, or in the alternative, different Weighting Factor—Session Duration relations can be used to select the Weighting Factor for a Usage Session Value depending on the presence, number, and/or severity of the respiratory event detected during a Usage Session. These different relations can be stored in a memory and the appropriate relation selected based on the monitored parameter.

For example, if one or more snoring or apnea events are detected during a Usage Session, the Weighting Factor for that Usage Session can be reduced. This is logical as the presence of snoring or apneas tends to indicate a lack of effectiveness of the pressure support treatment. The amount of reduction can be based on any desired criteria, such as the number of snoring or apnea events detected, their severity, or frequency.

A further embodiment of the present invention contemplates monitoring the medical device or the treatment being provided by the medical device and adjusting the Weighting Factor for that Usage Session based on the monitored condition medical device or the treatment being provided. This can be done alone or in combination with monitoring the physiological condition of the patient during a Usage Session and adjusting the Weighting Factor for that Usage Session based on that monitored condition.

For example, the present invention contemplates monitoring the amount or flow of gas leaking from the pressure support system. If this flow exceeds a predetermined threshold, the Weighting Factor can be adjusted using any of the techniques discussed above, because it is likely the patient is not receiving the optimum treatment from the pressure support system having such a relatively large leak. Similarly, the gas output by the pressure support system and/or the pressure at the patient can be measured directly or indirectly using any conventional technique. If one or both of these pressures is not within acceptable levels, the Weighting Factor can be adjusted using any of the techniques discussed above, because it is again unlikely that the patient is receiving the optimum treatment.

An apparatus capable of performing the above-described method is also contemplated by the present invention. Typically, the method of the present invention would be included as software installed on either medical device 12 or computing device 34. Specifically, as seen in FIG. 2, when using the illustrated pressure support system 14, the software would be installed on controller 28, communication device 32, and/or computing device 34. Of course, various portions of the compliance monitoring algorithm could be located at one or more of these respective components.

The above-discussed data and compliance information can be: (1) located on medical device 12, typically the controller 28; (2) displayed on display device 30 of the medical device; (3) transmitted by medical device 12 to central database 36; (4) transmitted from the medical device by a communication device 32 (such as a modem) to the central database; (5) transmitted from the medical device to a transmittable medium of storage (such as a diskette or smart card), and thereafter transferred to the central database; and/or (6) transmitted by the medical device via communication device 32 to remote computing device 34, which contains the central database 36.

In an exemplary embodiment of the present invention, communication device 32 includes the components necessary to perform the data processing and storage functions to carry out the compliance and short session monitoring techniques of the present invention. The input data indicative of usage of the pressure support system is supplied by controller 28 to communication device 32. This embodiment is advantageous in that the basic pressure support system can be built without the additional components necessary to carry out the compliance and short session monitoring techniques of the present invention. This is desirable because there may be instances when such functions are not desired in the basic pressure support system.

When these functions are desired, communication device 32 capable of implementing these functions can be readily provided, for example as a modem, by attaching the modem to a data terminal on the pressure support system. This modem functions as a "smart modem" in that it receives the device usage indication from the pressure support system and performs the compliance and short session monitoring techniques of the present invention. The modem can then download this data to a remote location. The thresholds used by the compliance and short session monitoring techniques of the present invention, such as the Compliance Period, Medical Device Usage Prescription Value, Measurement Cycle, Compliance Warning Value, etc., can be provided to the modem using any conventional technique. However, it is advantageous to allow the modem to receive such threshold values from the remote location so that they can be readily adjusted and monitored.

In the embodiments discussed above, the usage of the medical device is measured based on time, e.g., how many minutes the system is used. This requires providing a timing device, such as a clock, to make this determination. The present invention, however, contemplates that the usage of the medical device can be measured based on criteria other than time. In one embodiment, the usage of the medical device is based on number of breathing cycles detected. For example, during a Usage Session, the system monitors the number of breathing cycles experienced by the patient. This number of breathing cycles can be used in place of time to determine the count of Short Sessions or to determine any Weighting Factor to be applied against to the Session Usage Value, which in this embodiment is a numerical indication of the number of respiratory cycles experienced by the patient during the Usage Session. Similarly, the Compliance Period and Measurement Cycle can be set based on breathing cycles.

Overall, the present method and system yield an effective and accurate manner of tracking and monitoring patient compliance with a medical device usage prescription or regimen. The present method can be used to determine compliance, non-compliance or other levels of compliance or warning states. The present method will assist the doctor, caregiver, etc. in making an assessment of just how compliant a patient is with his or her medical device usage. The present method will also allow the doctor or caregiver to realistically assess the effectiveness of the medical device usage prescription. In addition, the present method includes steps that take into account the diminishing effect of a short session usage of the medical device.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

DEFINITION OF TERMS USED IN THE SPECIFICATION

The following is a listing of the terms used in the above specification. This listing is intended to supplement and not replace the definition of the terms given above, as understood by those skilled in the art based on the context in which they are presented, but may serve to help clarify the intended meaning of each.

Compliance Period—period of time over which one or more Usage Sessions are monitored and accumulated, typically one day.

Usage Session—a period of time, typically expressed as a number of minutes or hours, during a Compliance Period in which the medical device is used in a continuous basis by the patient.

Medical Device Usage Prescription Value—period of time, typically expressed as a number of hours, that the medical device should be used by the patient during a Compliance Period.

Minimum Medical Device Usage Compliance Value—minimum level of usage required during a Compliance Period, below which the benefit of the medical device begins to diminish.

Measurement Cycle—period of time or number of Compliance Periods over which the patient is to be monitored to indicate actual compliance with the prescribed therapy.

Compliance Period Value—number of Compliance Periods in the Measurement Cycle in which an Actual, i.e., measured, Medical Device Usage Value is equal to or greater than the set Minimum Medical Device Usage Compliance Value Actual Medical Device Usage Value—actual measurement of device usage obtained using any conventional technique for monitoring device usage.

Measurement Cycle Compliance Value—a value, typically a percentage or period time, during the Measurement Cycle, below which the benefit of the medical device begins to diminish.

Compliance Indicator—a signal provided in any conventional format indicative of some measure of the compliance of the patient, such as "compliant," "non-compliant", "marginally compliance", "compliant—but trending toward non-compliance", "non-compliant—but tending toward compliance", etc.

Compliance Warning Value—a warning threshold that is compared with the Compliance Period Value, where a deviation of the Compliance Period Value below this threshold indicates that a warning of "lack of compliance warning" should be issued.

Actual Medical Device Session Usage Value—a period of time that corresponds to each Usage Session.

Weighting Factor—A multiplier assigned to an Actual Medical Device Session Usage Value based on the length of time of the Actual Medical Device Session Usage Value.

Minimum Medical Device Usage Short Session Value—period of time for a Usage Session that, if not exceeded, causes that Usage Session to be considered as a Short Session.

Short Session Count Value—a count of the number of Short Sessions occurring during a Compliance Period.

Short Session Warning Value—a warning threshold that is compared with the Short Session Count Value, where a deviation of the Short Session Count Value to a value that is equal to or greater than this threshold indicates that a warning should be issued, such as a warning indicating that short sessions are occurring.

What is claimed is:

1. A method for tracking and monitoring a patient's compliance with a prescription for a medical device during a compliance period, the method comprising:
executing one or more computer program modules using one or more processors to cause the one or more processors to:
receive a minimum medical device usage short session value;
determine an actual medical device usage value for at least one discrete medical device usage session associated with a medical device adapted to provide a treatment to a patient;
compare the actual medical device usage value for each medical device usage session with the minimum medical device usage short session value; and
determine an actual medical device usage value for the compliance period by summing the actual medical device usage value for each medical device usage session that is greater than or equal to the minimum medical device usage short session value and subtracting each actual medical device usage value that is less than the minimum medical device usage short session value during the compliance period.

2. The method of claim 1, wherein the one or more processors are further caused to:
apply a weighting factor to the actual medical device session usage value to produce a weighted actual medical device session usage value for the at least one medical device usage session;
wherein summing the actual medical device usage for each medical device usage session includes summing the weighted actual medical device usage values for the medical device usage sessions during the compliance period.

3. The method of claim 2, wherein the weighting factor is variable dependent upon the actual medical device session usage value.

4. The method of claim 3, wherein the weighting factor is in a range from 0 to 1.

5. The method of claim 1, wherein the one or more processors are further caused to:
determine a short session count value based upon the number of usage sessions wherein the actual medical device usage value for the respective usage session is less than the minimum medical device usage short session value.

6. The method of claim 5, wherein the one or more processors are further caused to:
provide a short session warning value to the medical device;
compare the short session count value with the short session warning value; and
provide a warning signal for presentation responsive to the short session count value being equal to the short session warning value.

7. A system configured for tracking and monitoring a patient's compliance with a prescription for a medical device during a compliance period, the system comprising:
one or more processors configured to:
monitor an actual medical device usage for at least one discrete medical device usage session associated with a medical device adapted to provide a treatment to a patient;
compare the actual medical device usage value for each medical device usage session with a minimum medical device usage short session value; and
determine an actual medical device usage value for the compliance period by summing the actual medical device usage value for each medical device usage session that is greater than or equal to the minimum medical device usage short session value and subtracting each actual medical device usage value that is less than the minimum medical device usage short session value during the compliance period.

8. The system of claim 7, wherein the one or more processors are further configured to determine a compliance period value as a number of compliance periods in a measurement cycle in which the actual medical device usage value is at least equal to a minimum medical device usage compliance value.

9. The system of claim 8, wherein the one or more processors are further configured to compare the compliance period value with a medical device usage prescription value.

10. The system of claim 8, wherein the one or more processors are further configured to determine the compliance period value as a percentage of compliance periods in the measurement cycle in which the actual medical device usage value is at least equal to the minimum medical device usage compliance value.

11. The system of claim 8, wherein the one or more processors are further configured to:
compare the compliance period value with a measurement cycle compliance value; and
output a compliance indicator based upon results of the comparison.

12. The system of claim 11, wherein the compliance indicator indicates one or both of: (1) a compliance signal responsive to the compliance period value being at least equal to the measurement cycle compliance value, or (2) a non-compliance signal responsive to the compliance period value being less than the measurement cycle compliance value.

13. The system of claim 11, wherein the compliance indicator indicates a compliance signal, a non-compliance signal, a marginal compliance signal, a warning signal, a trend signal, a compliance value signal, or any combination thereof.

14. The system of claim 11, wherein the one or more processors are further configured to provide a report based upon the compliance indicator and indicative of at least one patient's compliance with at least one of a medical device usage prescription value, a minimum medical device usage value, or a measurement cycle compliance value.

15. The system of claim 8, wherein the one or more processors are further configured to:
compare the compliance period value with a compliance warning value; and
provide a warning signal for presentation to a user responsive to the compliance period value being equal to the compliance warning value.

16. The system of claim 7, wherein the medical device includes one or more of a ventilator, a pressure support system, an oximeter, a ventilatory support system, an oxygen concentrator, a nebulizer, a humidifier, a phototherapy device, an immersion therapy device, or a physical therapy device.

17. The system of claim 7, wherein at least one of the one or more processors are resident in the medical device.

18. The system of claim 7, further comprising a communication device associated with the medical device, and wherein at least one of the one or more processors is resident in the medical device and at least one of the one or more processors is resident in the communication device.

19. The system of claim 7, further comprising:
a communication device associated with the medical device; and
a central database remote from the medical device and in communication therewith via the communication device.

20. The system of claim 7, wherein the one or more processors are further configured to apply a weighting factor to the actual medical device session usage value.

21. The system of claim 20, wherein the weighting factor is variable dependent upon the actual medical device session usage value.

22. The system of claim 20, wherein the weighting factor is in a range from 0 to 1.

23. The system of claim 7, wherein the one or more processors are further configured to:
receive the minimum medical device usage short session value; and
determine a short session count value based upon the number of usage sessions wherein the actual medical device usage value for the respective usage session is less than the minimum medical device usage short session value.

24. The system of claim 23, wherein the one or more processors are further configured to:
compare the short session count value with a short session warning value; and
provide a warning signal for presentation to a user responsive to the short session count value being equal to the short session warning value.

* * * * *